Figure 1:
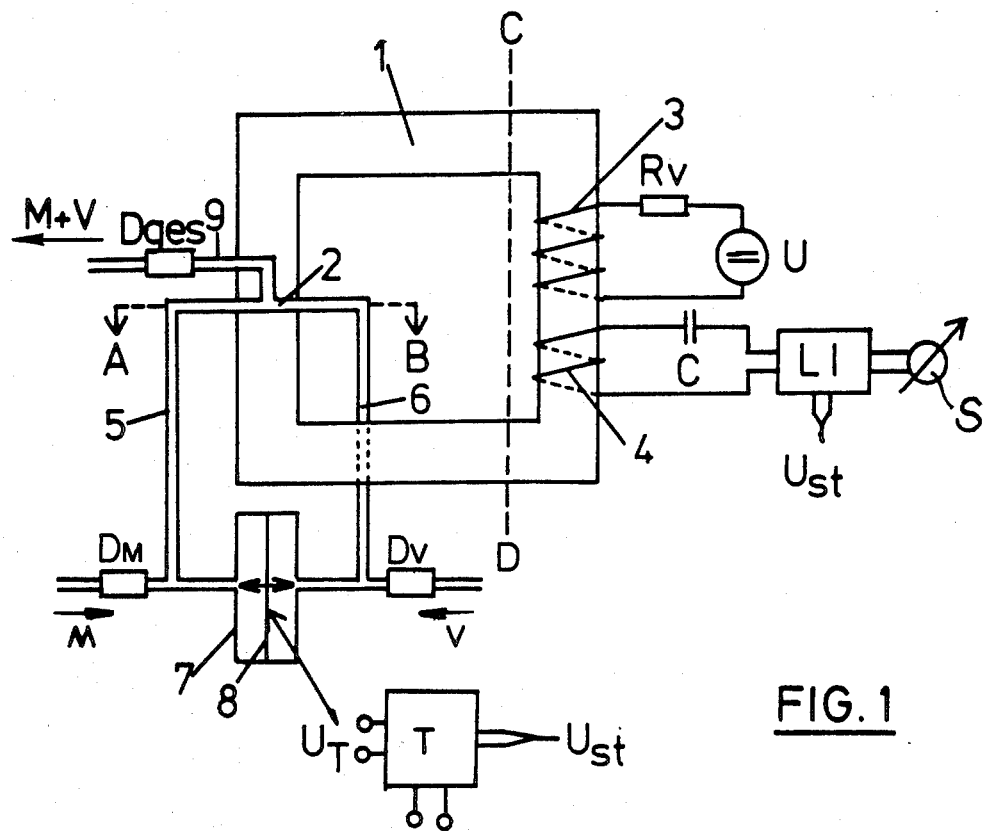

United States Patent [19]

Hummel

[11] Patent Number: 4,683,426

[45] Date of Patent: Jul. 28, 1987

[54] PROCESS AND APPARATUS FOR MEASURING DIFFERENCES IN THE CONCENTRATIONS OF PARAMAGNETIC COMPONENTS OF GASES

[75] Inventor: Heinz P. Hummel, Königstein-Johanniswald, Fed. Rep. of Germany

[73] Assignee: Leybold-Heraeus GmbH, Cologne, Fed. Rep. of Germany

[21] Appl. No.: 659,269

[22] Filed: Oct. 10, 1984

[51] Int. Cl.⁴ .............................................. G01R 33/12
[52] U.S. Cl. .................................... 324/204; 73/27 A
[58] Field of Search ................. 324/204, 201; 73/27 A

[56] References Cited

U.S. PATENT DOCUMENTS 3,049,665  8/1962  Hummel .............................. 324/204
3,584,499  6/1974  Hummel ................................. 73/23

FOREIGN PATENT DOCUMENTS 1149187  5/1963  Fed. Rep. of Germany .
1648924  8/1967  Fed. Rep. of Germany .

Primary Examiner—Reinhard I. Eisenzopf
Assistant Examiner—Robert W. Mueller
Attorney, Agent, or Firm—Felfe & Lynch

[57] ABSTRACT

Process and apparatus for measuring the difference in the concentration of paramagnetic components between an unknown gas and a standard gas by periodically alternate entry of both gases into the gap chamber (2) of a magnetic circuit (1) and by detecting the periodical variations of the magnetic flux caused by the gases in the magnetic circuit.

In this process,
(a) the two gases are brought into the gap chamber (2) from opposite directions through gas lines (5, 6),
(b) the boundary zone between the two gases perpendicular to the magnetic lines of force is moved back and forth in the gap chamber periodically by an alternating flow generator (7), and
(c) constantly a portion of the gas mixture is made to escape through an exhaust line (9) from the region of the gap chamber (2) by the inflowing of at least one of the two gases.

6 Claims, 11 Drawing Figures

PROCESS AND APPARATUS FOR MEASURING DIFFERENCES IN THE CONCENTRATIONS OF PARAMAGNETIC COMPONENTS OF GASES

The invention relates to a process for measuring differences in the concentration of paramagnetic particles in a gas being measured and in a standard gas by the periodic alternate passing of the two gases into the air gap of a magnetic circuit and detecting the periodic changes caused by the gases in the magnetic flux of the magnetic circuit.

The gases in question are, depending on the circumstances, either pure gases or mixtures of gases. Such a process is disclosed in U.S. Pat. No. 3,049,665. By the periodic alternating filling of a magnetic gap with a standard gas of known composition and a gas of unknown composition, a periodic alternating magnetic flux is produced, which is used as a measure of the difference in the concentration of paramagnetic components in the unknown gas. The known process has substantial disadvantages. Controlled valves or gas switchers are used for the production of the alternating filling. This is disadvantageous with regard to the expense involved and the liability of such elements to trouble. For example, at a technically desirable modulation frequency of 25 Hertz, the number of reversals in a year of operation is approximately $800 \times 10^6$. Moreover, in the systems in question, the measuring gap chamber including the feed lines has to be scavenged with large volumes of fresh gas (the unknown gas or standard gas) upon each alternate filling. Assuming a volume of 1 cubic meter for the gap chamber and feed line, and the above-stated frequency of 25 Hertz, the consumption would amount to 90 liters per hour. This is undesirable on the one hand on account of the need to have of large amounts of the standard gas (approximately 800 cu.m. per year) available, and on account of the entry of dirt into the switching valves and into the measuring gap chamber which the throughput of the unknown gas necessarily entails, which then leads to very stringent requirements with regard to the preparation of the samples. This sample preparation, in addition to the investment and maintenance costs, lengthens the time required for the measurement. This signifies an additional disadvantage. The gas stream is periodically interrupted by the valves or gas switchers, and all of the gas that is in the piping system has to be scavenged out repeatedly, but completely. The same U.S. Pat. No. 3,049,665 furthermore discloses the subjecting of the unknown gas to a so-called pressure modulation and the measurement of the effects of periodical pressure changes on the magnetic flux in the gap chamber. This process, however, has still more disadvantages:

1. If it were desired to achieve by the alternating pressure the same measuring effect as in alternate filling, it would be necessary to operate with an excess pressure of at least about one bar. At this pressure, the magnetic flux changes caused by mechanical deformation of the gap would be very disturbing and could not be avoided without very expensive cellular designs; at the same time it is to be noted that, at a sensitivity of detection commonly required of such apparatus of about 1 per mill of oxygen, a magnetic flux change of 2.10 is the result. Gap changes due to deformation, however, produce many times this amount of flux change.

2. The means for the production of a constant amplitude of pressure alternation are very expensive. Furthermore, the pressure amplitude is affected by the composition of the unknown gas.

3. Feeding the system with the unknown gas requires an elevated unknown-gas pressure.

German Pat. Nos. 1,149,187 and 1,648,924 also disclose a kind of inversion of the measurement principle, in which periodical changes in the magnetic field strength provoke proportional pressure variations in the gases, which are a measure of the percentage of the paramagnetic components. The necessary alternating field magnetization represents an additional expense, aside from the high heat losses which result if the alternating flux intensities are sufficiently great.

The invention is addressed to the problem of reducing the consumption especially of the standard gas and reducing the throughput of possibly dirty unknown gas, as well as increasing responsiveness and accuracy of measurement while reducing the cost of the apparatus.

The solution of the stated problem is achieved in accordance with the invention, in the process described above:

(a) by delivering the two gases into the air gap alternately from opposite directions, (b) moving the boundary zone between the two gases back and forth periodically in the air gap perpendicularly to the magnetic lines of force, and (c) constantly causing part of the gas mixture to escape from the air gap region by letting at least one of the two gases flow in behind it.

The system of the invention differs very advantageously from the process in which the alternating pressure in an alternating magnetic field is measured, in that the very expensive and delicate alternating pressure receivers are avoided. One great advantage of the method of the invention is the extremely brief time delay involved in the measurement. The following advantages of the invention are especially to be stressed:

1. The means for producing the alternating filling are comparatively very simple and also very reliable in constant operation.

2. As it will be seen in the systems explained further below, the consumption of the unknown gas and the standard gas is very low, because in the system dynamically shut off by flow throttling, only the volume of gas enclosed in the system, which is dynamically sealed by throttles, oscillates (pulsates) back and forth. Fresh gas is constantly fed in only for the purpose of maintaining the boundary zone between the unknown and standard gas, which otherwise is blurred by diffusion, and, as far as the unknown gas is concerned, for the purpose of adapting the filling of the gap to the particular state of the unknown gas at a gas concentration that varies with time.

3. On account of Point 2, changes in the rate of flow in the incoming unknown gas and standard gas have no effect on the time required for the alternating filling.

4. In the known methods of alternate filling, an alternating pressure is produced by the resistance to flow on account of the necessary great amount of flow in the measuring gap. This is virtually eliminated in the system of the invention.

The invention also relates to an apparatus for the performance of the process of claim 1, having a gap chamber which is formed within the air gap of the magnetic circuit and is connected by at least one gas line to an alternating flow generator for the alternating injection of the unknown and standard gas and which has at least one exhaust line, and having at least one winding for the detection of the periodic changes of the magnetic flux in the magnetic circuit. For the solution of substantially the same problem, this apparatus is characterized in accordance with the invention in that (a) The gap chamber is provided on two opposite sides with at least one gas line each, of which one is the unknown gas feed line and the other the standard gas feed line, (b) By means of the alternating flow generator, such a gas volume can be moved that the gap chamber can be filled substantially with the unknown gas or with the standard gas with periodic alternation, and (c) The at least one exhaust line is always in communication through the gap chamber with at least one of the two gas lines.

If this design specification is fulfilled, the result will be that the gas-charged part of the measuring system can be made very simple and sturdy both as regards manufacture and as regards adjustment and operation. The requirements to be met by the measuring electronics are approximately the same as those in the alternating pressure method (e.g., German Federal Pat. Nos. 1149187 and 1648924). The power supply electronic circuitry is comparatively very simple, because the electrical power necessary for the alternating flow generator is a multiple lower than in the case of the supplying electrical power to a magnetic circuit of high alternating flux density. The power necessary for the DC field excitation is likewise comparatively very small, quite aside from the possibility of permanent magnet excitation.

It is especially advantageous if the alternating flow generator is disposed between the gas lines and has two chambers separated by a membrane, of which one is connected to the unknown gas line and the other with the standard gas line, such that unknown gas and standard gas can be introduced into the gap chamber and removed again therefrom rhythmically by a periodic oscillating movement of the membrane. However, a variety of other systems available as technical components can serve as alternating flow generators, such as electromagnetic telephones (or loudspeakers), electrodynamic telephones, electrostatic microphones, magnetostrictive sound generators, thermophones, electromagnetic membrane pumps (after removal of the valves) and other corresponding components known in the state of the art, such as mechanically powered membrane or piston generators. Frequencies between 1 and 100 Hz, preferably between 10 and 50 Hz, have proven useful as alternation frequencies for the pumping effect.

To minimize the gas throughput and for the production of definite gas flows, it is furthermore advantageous for a throttle to be disposed both in the lines feeding the gas lines and in the at least one exhaust line. If provision is made so that the sum of all flow cross sections downstream is always greater than the sum of all flow cross sections upstream, undesirable pressure fluctuations are effectively prevented by varying the amounts of the gas. The throttling effect can also be achieved by means of gas lines having small flow cross sections. In any case, however, care must be taken to see that the flow cross sections in the section of the apparatus in which the gases oscillate back and forth, or the flow cross sections in which the gases oscillate in a circuit separated only by the membrane, are comparatively larger, so that no appreciable resistance to flow will be present.

Figure 4:
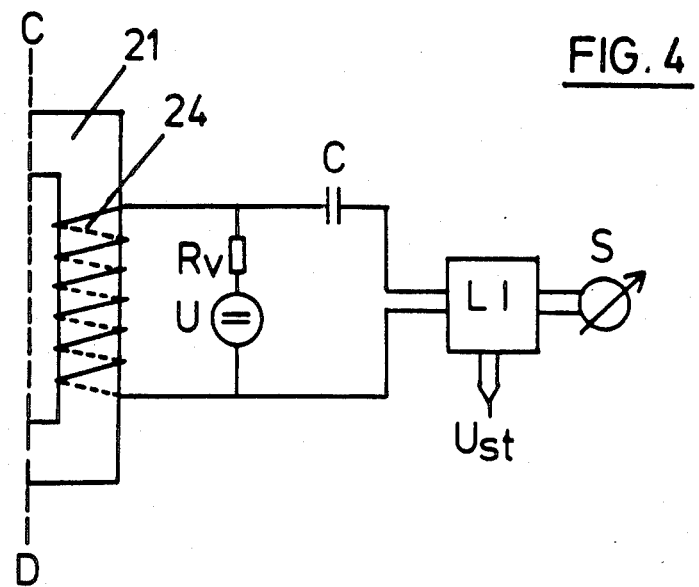
Figure 5:
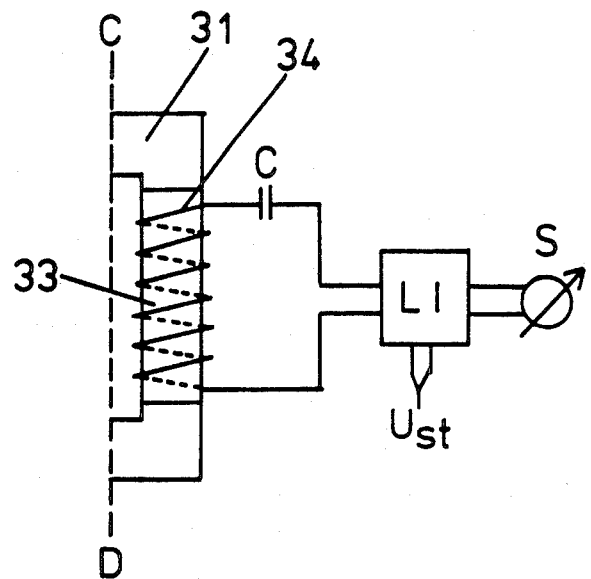

Exemplary apparatus in accordance with the invention are diagrammatically represented in FIGS. 1 to 3 and 6 to 7. FIGS. 4 and 5 represent other possibilities for the electrical circuitry. FIGS. 8a to 8b show exemplary embodiments of alternating flow generators, and FIGS. 8c and 8d show two additional possible embodiments of the apparatus for the alternating filling.

The variants described in U.S. Pat. No. 3049665, namely the use of a high-frequency field, use of a permanent magnet, and construction as a pot magnet system, apply accordingly also to the system of the invention. It is possible to construct the magnetic circuit of a soft iron core with an exciter winding, or to provide a permanent magnet within the soft iron core. Therefore, mention thereof in all their details is superfluous.

FIG. 1 shows a system having a double alternating flow generator (bilaterally acting alternating flow generator) and a DC-excited magnetic circuit 1. This circuit consists of a magnetic core composed of 2 parts having a gap chamber 2. The magnet core is made of soft-magnetic band material and has a square cross section of 1 cm$^2$. The gap width amounts to 0.3 mm. The magnet is excited by the winding 3, which is supplied with direct current through the DC source U and a series resistance Rv. The resistance Rv is intended to prevent the alternating voltage produced in the winding by alternating filling modulation from being short-circuited. Instead of the series impedance an inductive resistance can be used. The gap chamber 2 is connected by the gas lines 5 and 6 to the alternating flow generator 7 with the vibratable membrane 8. The feeding of unknown gas (M) and standard gas (V) is performed through the two throttles Dm and Dv. The unknown gas and the standard gas are exhausted from the gap chamber 2 from a central bore through the exhaust line 9 and the throttle Dges.

Figure 2:
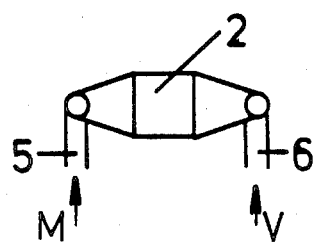
Figure 3:
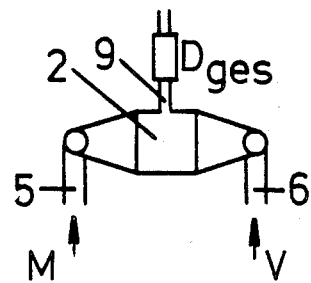

FIGS. 2 and 3—sections along line A–B in FIG. 1—are intended to show how the tubular gas lines (inside diameter about 2 mm) are connected on approximately equal cross sections to the gap chamber 2 by transitions which continuously flare in one plane and continously taper in the plane perpendicular thereto. FIG. 3 shows a different embodiment for the common exhaust from the gap chamber.

The gap chamber 2 is formed by a chamber which, except for the gas feed and exhaust lines, is completely enclosed and defined by plane-parallel walls through which the magnetic lines of force pass perpendicularly. This chamber is inserted with a close fit into the air gap of the magnetic circuit.

The membrane 8 is excited to periodic oscillations with a frequency of 25 Hertz by the tone generator T powered from the electrical mains. The amplitude of the oscillations is such that the resultant volume-stroke suffices to refill the gap chamber (volume 30 cu.mm.) with the unknown gas or the standard gas. The arrow drawn from the tone generator voltage Ut to the membrane is intended to indicate the effect (see explanation of FIG. 8a). The control voltage Ust, whose frequency is equal to that of Ut (in a fixed phase relationship to Ut), serves for the control of the lock-in amplifier LI.

A second winding 4 on the magnetic core serves for the measurement of the alternating magnetic flux produced by the alternating filling modulation. The alternating voltage induced by this flux is delivered through the condenser C to the LI amplifier and, after amplification and rectification, is measured at the instrument S. The reading of the instrument is then a measure of the difference of the concentration of paramagnetic substance (generally oxygen) between the unknown gas and the standard gas. Since the standard gas is of known composition, the content of paramagnetic gas in the unknown gas can be determined.

FIG. 4 represents a variant of FIG. 1 in the electrical part. The part not shown (to the left of line CD) is entirely the same as in FIG. 1. Here only one winding is used on the magnet core 21, and serves simultaneously for the field excitation (through the DC source U and the input resistance Rv) and for alternating voltage measurement (coupling to the lock-in amplifier LI through the condenser C.

FIG. 5 is derived from FIG. 4. The DC excitation has been eliminated. A permanent magnet 33 in the magnetic circuit (magnetic circuit 31) produces the magnetic steady flux. The alternating voltage induced in the winding 34 is measured as in FIG. 4.

Figure 6:
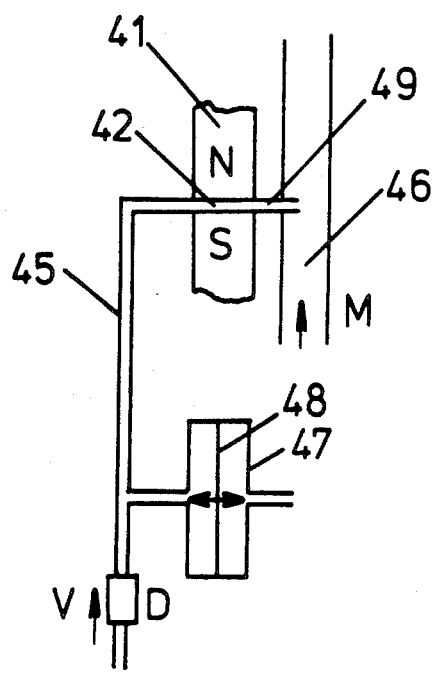

FIG. 6 shows a system which uses an alternating flow generator 47 with a membrane 48, and which acts unilaterally. The side that is not connected to the system is vented to the atmosphere. The standard gas is fed into the gap chamber 42 through the throttle D and the gas line 45, and emerges from the chamber through the very short gas duct 49 (nipple or slotted fitting of the smallest possible volume) into the gas line 46 through which the unknown gas is flowing and which in turn leads to the free atmosphere. The gap chamber 42 is situated in the magnet core 41, which is similar to the one in FIGS. 1 to 5. The alternating flow generator 47 connected to the gas line 45 periodically aspirates the unknown gas from the gas line 46 through the gas line 49 into the gap chamber 42 and displaces it again (in the same rhythm or counter-phase rhythm) with the standard gas. The system of FIG. 6 is distinguished from the system of FIGS. 1 to 5 by a very simple construction; this is especially the case with the gap chamber 42. The consumption of standard gas in this system of FIG. 6 is indeed greater than in the system of FIG. 1, yet it is still substantially lower than in the known systems.

It is true in this system as in all the other systems described in this specification that the feed of the unknown gas and standard gas can be changed around without affecting the absolute magnitude of the measurement effect.

Figure 7:
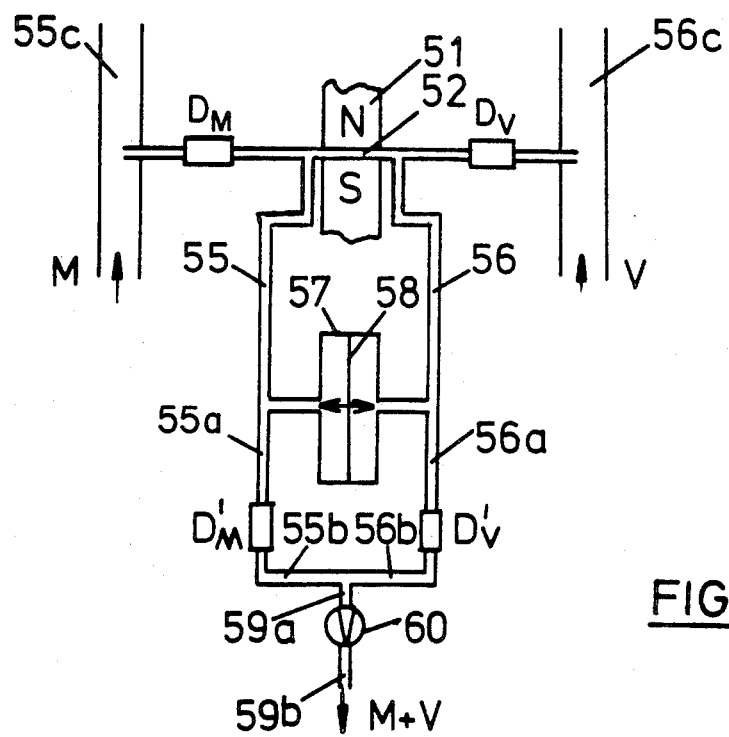
Figure 8A:
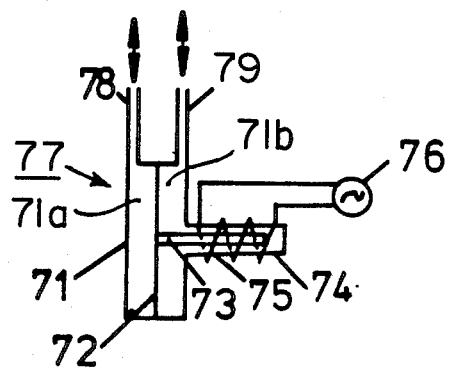
Figure 8B:
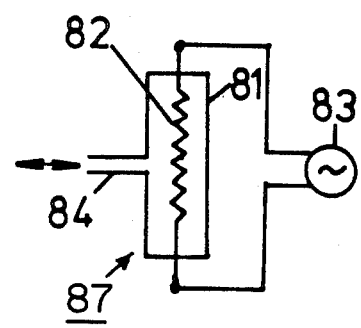
Figure 8C:
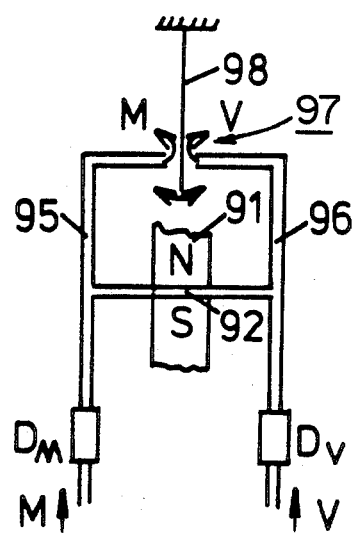
Figure 8D:
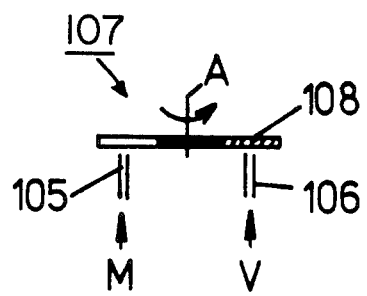

In FIG. 7 is described a system which develops from the system in FIG. 1 if the common exhausting of the unknown and standard gases is not performed directly from the gap 52. The exhausting of the unknown and standard gases from the alternating flow system formed by the gap 52, gas lines 55 and 56 and the alternating flow generator 57 with membrane 58—which is cut off from the outside dynamically by the throttles Dm and Dv—is first performed separately through the line sections 55a and 56a (with the throttles Dm' and Dv') and then together through the gas line 59a, the aspirating pump 60 and the exhaust line 59b. The charging of the entire system with the unknown gas and the standard gas is performed by aspiration from the lines 55c and 56c through which the unknown gas and standard gas, respectively, flow. These lines discharge into the free atmosphere.

FIG. 8a shows the exemplary construction of an alternating flow generator 77. The elastic, gas-tight membrane 72 is situated in a cylindrical casing 71 (cylinder axis lying in the plane of the drawing). The excitation of the membrane is performed by means of a ferromagnetic rod 73 (which can also be magnetized) surrounded by a nonmagnetic guard tube 74. This rod is excited to vibration by the alternating field (AC source 76) produced in the winding 75. The casing 71 with the two chambers 71a and 71b has the two connecting nipples 78 and 79 for the transmission of the volume shifts thus produced.

FIG. 8b shows an alternating flow generator 87 operating on the thermophone principle. A thin wire or a coil 82 consisting of thin wire is tensed in the cylindrical casing 81. A low-frequency alternating current (frequency 5 Hertz, for example), or a pulsating direct current, is flowing from the AC voltage source 83. The periodic heating of the wire which occurs, and the air surrounding the wire, produce periodical pressure fluctuations, resulting in pulsating currents which are fed through the nipple 84 on the open side of the alternating flow generator 47 in FIG. 6.

FIG. 8c shows another form of alternating flow modulation using an alternating flow generator 97 which has a vibrating leaf spring 98 (plane of vibration perpendicular to the plane of the drawing). The elements Dm, Dv, 92, 95 and 96 correspond to those of FIG. 1, but the gap chamber 92 does not have a separate outlet nipple. The magnetic circuit 91 is the same as in FIG. 1 (only a portion being indicated). The orifices of the gas lines 95 and 96 are disposed with respect to one another and to the leaf spring 98 such that, when the leaf spring vibrates, first the gas line 95 is closed, and then, one-half period later, the gas line 96 is closed. In the first case, when the gas line 95 is closed, the unknown gas M flows through the gap chamber 92, and in the second case the standard gas V. The leaf spring is driven magnetomechanically, for example, and the alternating voltage required for this purpose is used for controlling the amplification (as described above).

Another method of alternating filling by an alternating flow generator 107 is shown in FIG. 8d. For the periodic, counter-phase opening and closing of the gas lines 105 and 106 (which correspond to the gas lines 95 and 96 in FIG. 8c) it uses a synchronously rotating segmented disk 108 or a perforated disk or the like disposed in front pf the gas lines and having the drive axis A. Instead of this disk, a rotating toothed wheel can be used, while the gas lines 105 and 106 are disposed directly in front of the outer crown of teeth, and are offset by the distance of half a tooth.

It is also possible to operate the alternating fill modulation without any especially prepared standard gas. In this case the standard gas is formed from a partial stream of the unknown gas by heating this partial stream immediately before it enters into the gap chamber, to a given temperature of, say, 100° C. At the point of a concentration gradient in the boundary zone between the two gases, which is moved periodically back and forth perpendicular to the magnetic lines of force in the air gap, a temperature gradient is produced which has a comparable effect, since the parametric properties of the gases or gas components herein involved change considerably with the temperature.

For this purpose it is necessary to divide the unknown gas stream into two partial streams M and V through two throttles. Partial stream M is fed directly to the gap chamber, as in FIG. 1, and partial stream V through a heated section of pipe. The difference in the paramagnetic effect, which is temperature-related, is measured and serves, according to the temperature difference between M and V, for measuring the content of paramagnetic substance in the unknown gas (see also U.S. Pat. No. 3584499 in this regard).

While in the case of the alternating flow generators 7, 47, 56 and 77, using a membrane and two chambers separated by the membrane, the oscillating gas volume is determined by the rate of delivery of the membrane (or piston), in the case of an alternating flow generator 97 using a leaf spring, it is the frequency of oscillation of the leaf spring in conjunction with the individual gas flows which determines the magnitude of the oscillating gas volume. Similar considerations apply to the alternating flow generator 107 of FIG. 8d, in which the leaf spring is replaced by open or closed segments of the segmented disk 108.

I claim:

1. A method of measuring a difference in concentration of paramagnetic components between an unknown gas and a standard gas comprising:
   periodically alternating entry of two gases into an air gap of a magnetic circuit by delivering the two gases into the air gap alternately from opposite directions;
   moving a boundary zone between the two gases back and forth periodically in the air gap perpendicularly to the lines of force;
   alternatingly causing part of the two gases to escape from the air gap region by letting the respective one or other of the two gases flow in behind the respective escaping gas; and
   detecting periodic changes, caused by the gases, in magnetic flux in the magnetic circuit.

2. Apparatus for performing a method of measuring a difference in concentration of paramagnetic components between an unknown gas and a standard gas comprising periodically alternating entry of two gases into an air gap of a magnetic circuit by delivering the two gases into the air gap alternately from opposite directions, moving a boundary zone between the two gases back and forth periodically in the air gap perpendicularly to the lines of force, constantly causing part of the two gases to escape from the air gap region by letting one of the two gases flow in behind the part of the two gases, and detecting periodic changes, caused by the gases, in magnetic flux in the magnetic circuit, the apparatus comprising:
   a magnetic circuit having an air gap and having a gap chamber formed within the air gap;
   an alternating flow generator for alternating injection of the unknown gas and the standard gas;
   at least one exhaust line coupled to the gap chamber;
   at least one winding for detecting periodic variations of the magnetic flux in the magnetic circuit;
   at least one gas line on each of two opposite sides of the gap chamber coupling the gap chamber to the alternating flow generator, of which one gas line is the unknown gas feed line and an other gas line is the standard gas feed line;
   the alternating flow generator moving such a gas volume that the gap chamber is filled substantially entirely with the unknown gas or with the standard gas with periodic alternation; and
   the at least one exhaust line being always in communication through the gap chamber with one of the two gases.

3. Apparatus in accordance with claim 2, in which the alternating flow generator is disposed between the gas feed lines and has two chambers separated by a membrane, of which the one chamber is connected to the gas line for the unknown gas and the other chamber to the gas line for standard gas, such that, by a periodically oscillating membrane movement, unknown gas and standard gas are introducible into the gap chamber and removable again therefrom in alternating rhythmn.

4. Apparatus in accordance with claim 3, which includes lines leading to the two gas feed lines and in which, both in the lines leading to the gas feed lines and in the at least one exhaust line there is disposed one flow throttle each.

5. Apparatus in accordance with claim 2, in which the alternating flow generator is of valve-less construction.

6. Apparatus in accordance with claim 2, in which the gas line of the gap chamber is scavenged by the unknown gas in the one period and by the standard gas in the other period.

* * * * *

UNITED STATES PATENT AND TRADEMARK OFFICE
CERTIFICATE OF CORRECTION

PATENT NO. : 4,683,426
DATED : July 28, 1987
INVENTOR(S) : Heinz P. Hummel

It is certified that error appears in the above-identified patent and that said Letters Patent is hereby corrected as shown below:

Column 4, line 28 for "impedance" read -- resistance --.

Column 4, line 29 for "resistance" read -- impedance --.

Signed and Sealed this

Eighth Day of August, 1989

Attest:

DONALD J. QUIGG

Attesting Officer

Commissioner of Patents and Trademarks